United States Patent [19]

Sinnreich

[11] 4,198,981
[45] Apr. 22, 1980

[54] INTRAUTERINE SURGICAL DEVICE

[76] Inventor: Manfred Sinnreich, 160 Fort Hill Rd., Scarsdale, N.Y. 10583

[21] Appl. No.: 887,261

[22] Filed: Mar. 27, 1978

[51] Int. Cl.² .................... A61M 29/02; A61M 25/00
[52] U.S. Cl. .................................. 128/344; 128/349 B
[58] Field of Search ................... 128/349, 349 B, 325, 128/349 R

[56] References Cited

U.S. PATENT DOCUMENTS

| | | | |
|---|---|---|---|
| 2,687,131 | 8/1954 | Raiche | 128/349 B |
| 2,854,982 | 10/1958 | Pagano | 128/349 BV |
| 3,050,066 | 8/1962 | Koehn | 128/325 X |
| 3,144,868 | 8/1964 | Jascalevich | 128/349 B |
| 3,882,852 | 5/1975 | Sinnreich | 128/344 X |

*Primary Examiner*—Stephen C. Pellegrino
*Attorney, Agent, or Firm*—Charles E. Temko

[57] ABSTRACT

An improved insufflating device particular adapted for use in intrauterine surgical procedures, and similar applications. The device is characterized in the provision of a first hollow shaft having an open distal end through which the barrel of an endoscopic or cystoscopic device is passed. A first inflatable balloon surrounds the shaft and serves to distend the lower portion of the uterus. A second balloon is mounted upon the distal end of a second hollow shaft fixed to the inner surface of said first shaft, and serves to distend the upper portion of the uterus, leaving a clear medially disposed circular area affording access to the lumen of the fallopian tubes for cauterization or other surgical procedure.

2 Claims, 3 Drawing Figures

INTRAUTERINE SURGICAL DEVICE

BACKGROUND OF THE INVENTION

This invention relates generally to the field of surgical instrumentation, and more particularly, to an insufflating device adapted for use in pneumatically expanding the uterus for intrauterine surgical procedures. Prior art devices of this type have included a relatively rigid hollow shaft, the outer surface of which mounts an inflatable balloon, which serves to distend the uterine walls. The end of the shaft is open, and permits the insertion of an endoscopic or cystoscopic instrument. Unfortunately, the performance of such devices has left much to be desired. Because the working area of the single balloon is generally below the end of the rigid tube, the upper end of the uterus must be distended by introducing unconfined air or other fluid which distends the uterus by virtue of the fact that the cervix is made fluid tight. However, the pressurized fluid is thereby forced into the fallopian tubes, with resultant frequent formation of embolisms and similar complications.

SUMMARY OF THE INVENTION

Briefly stated, the invention contemplates the provision in devices of this type of a second rigid tube which projects distally of the first tube and mounts on a distal end thereof a second balloon which is separately inflatable to expand the upper portion of the uterus and form, with the inflated first balloon, a clear generally annular interstice within which a surgical procedure may be performed. The air in both the first or lower balloon and the second or upper balloon is fully confined, and cannot reach the lumen of the fallopian tubes.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENT

Figure 3:
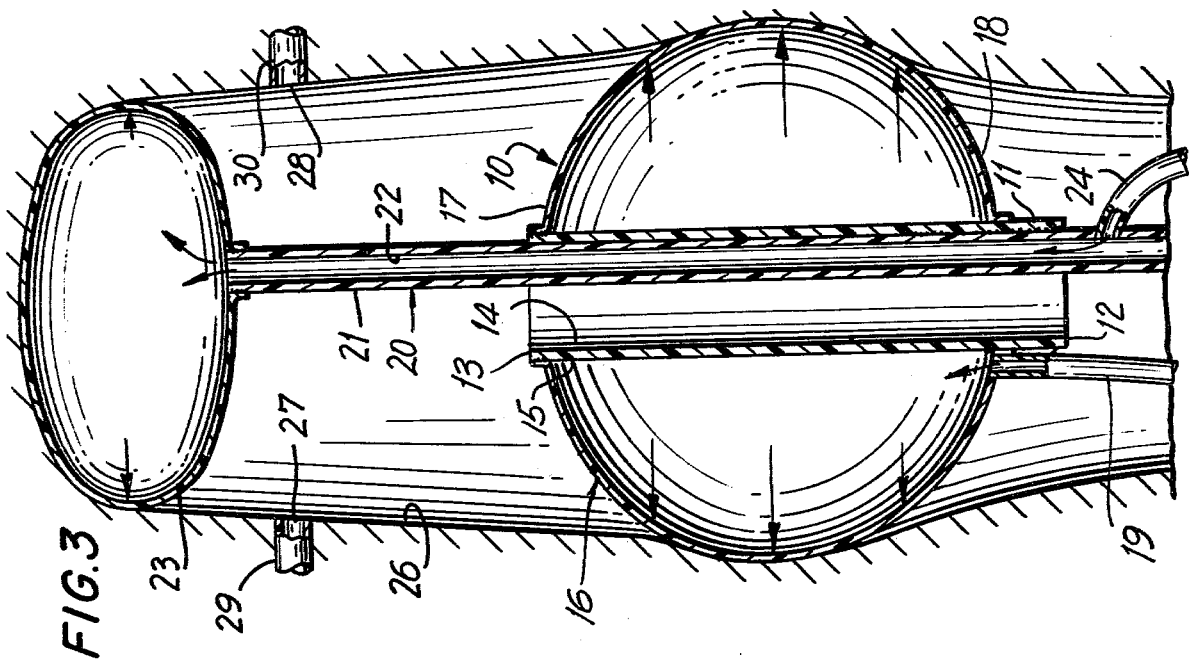
FIG. 3 is a similar fragmentary sectional view showing the embodiment in fully expanded condition prior to the commencement of a surgical procedure.

In accordance with the invention, the device, generally indicated by reference character 10, includes a first or outer relatively rigid shaft 11 having a proximal end 12 and a distal end 13 between which there extends a centrally disposed bore 14. The outer surface 15 mounts a first inflatable balloon 16 in a manner known in the art. As disclosed in my prior U.S. Pat. No. 3,888,852, granted 05/03/75, the balloon 16 includes upper and lowerr ends 17 and 18, respectively, which are sealed to the shaft 11. An inflation tube 19 connects with a source of compressed air.

Disposed within the bore 14 is a second or inner rigid shaft 20, the outer surface 21 being secured to a portion of the bore 14. The inner surface 22 defines a bore for inflating a second balloon 23 of shape resembling a mushroom cap. A separate inflating tube 24 communicates with the bore 22, and inflation of the two balloons is therefore separately controllable.

Figure 2:
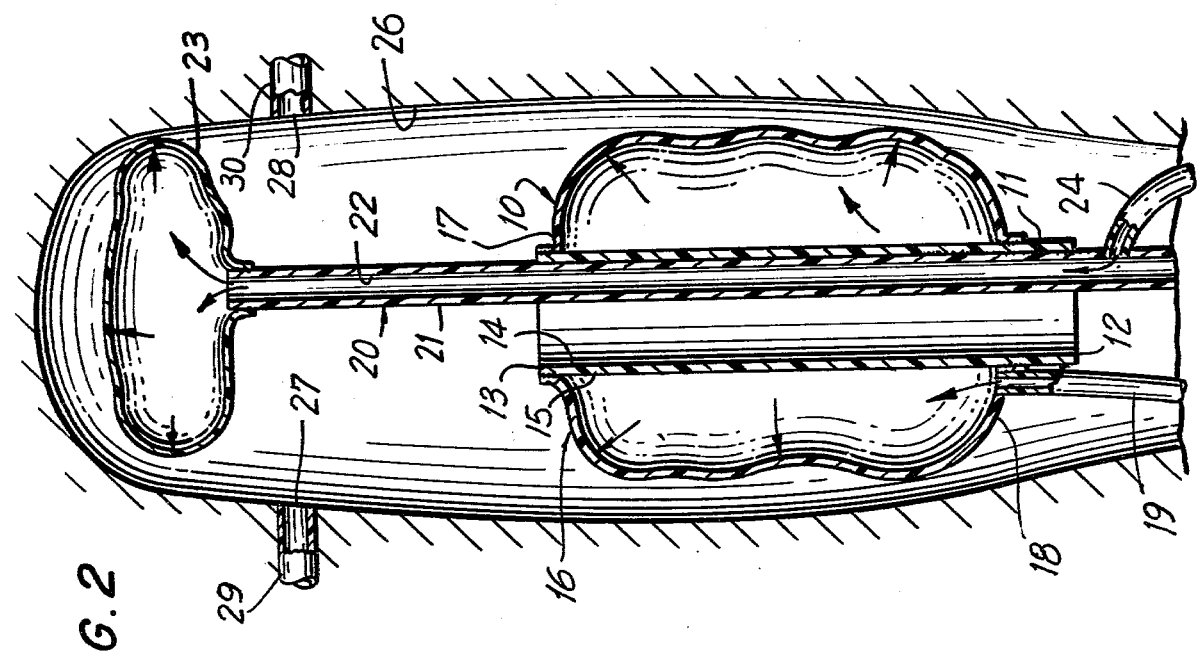
FIG. 2 is a fragmentary sectional view of the embodiment showing the same in inserted condition within the uterus, and partially inflated.
Figure 1:
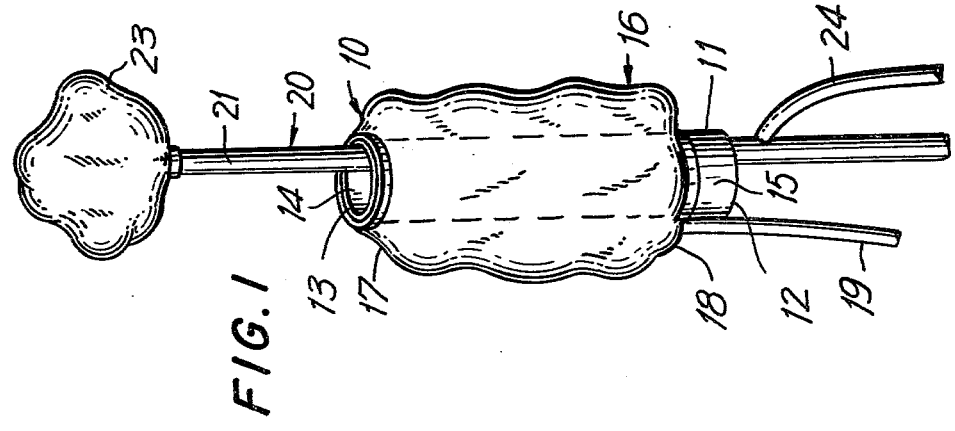
FIG. 1 is a fragmentary view in perspective of an embodiment of the invention, showing the same in relatively deflated condition prior to insertion.

Referring to FIG. 2, the device is illustrated in partially expanded condition after positioning within the uterus, at which point precise location may be accurately judged prior to full inflation. The device is located within the uterus 26 such that the lumen 27 and 28 of fallopian tubes 29 and 30 are positioned above the lower balloon and below the upper balloon, at which time full inflation is made prior to initiating the required surgical procedure.

When the procedure has been completed, both balloons are deflated, and the entire device withdrawn.

I wish it to be understood that I do not consider the invention limited to the precise details of structure shown and set forth in this specification, for obvious modifications will occur to those skilled in the art to which the invention pertains.

I claim:

1. An improved uterine insufflating device adapted to be positioned substantially entirely within the uterus of a patient, comprising: a first relatively rigid hollow shaft, a first inflatable balloon mounted on an outer surface of said first shaft between proximal and distal ends thereof; a second hollow shaft of diameter substantially less than the bore of said first shaft, sufficient to enable the introduction of a surgical instrument between said first and second shafts, and extending therethrough to project distally from the distal end of said first shaft, and a second inflatable balloon mounted on a distal end of said second shaft; whereby when said device is inserted within a uterus, and both balloons are inflated to expand the same, a clear generally annular interstice is formed between the balloons accessible from the distal end of said first shaft within which a surgical procedure may be performed.

2. A device as set forth in claim 1, further characterized in said second balloon being of generally hemispherical configuration when inflated.

* * * * *